United States Patent
Khalil et al.

(10) Patent No.: US 11,427,756 B2
(45) Date of Patent: Aug. 30, 2022

(54) SEMICONDUCTING LIGHT EMITTING MATERIAL

(71) Applicant: Merck Patent GmbH, Darmstadt (DE)

(72) Inventors: Sanaa Khalil, Jerusalem (IL); Kobi Oded, Jerusalem (IL); Denis Glozman, Modiin (IL); Ehud Shaviv, Modiin (IL)

(73) Assignee: MERCK PATENT GMBH, Darmstadt (DE)

( * ) Notice: Subject to any disclaimer, the term of this patent is extended or adjusted under 35 U.S.C. 154(b) by 0 days.

(21) Appl. No.: 16/755,181

(22) PCT Filed: Oct. 10, 2018

(86) PCT No.: PCT/EP2018/077540
§ 371 (c)(1),
(2) Date: Apr. 10, 2020

(87) PCT Pub. No.: WO2019/072882
PCT Pub. Date: Apr. 18, 2019

(65) Prior Publication Data
US 2021/0130684 A1 May 6, 2021

(30) Foreign Application Priority Data
Oct. 13, 2017 (EP) .................... 17196435

(51) Int. Cl.
| | |
|---|---|
| *C09K 11/02* | (2006.01) |
| *C07C 333/16* | (2006.01) |
| *C09K 11/08* | (2006.01) |
| *C09K 11/70* | (2006.01) |
| *C09K 11/88* | (2006.01) |
| *A61B 90/00* | (2016.01) |
| *H01L 33/50* | (2010.01) |

(52) U.S. Cl.
CPC .......... *C09K 11/025* (2013.01); *C07C 333/16* (2013.01); *C09K 11/0883* (2013.01); *C09K 11/703* (2013.01); *C09K 11/883* (2013.01); *A61B 90/36* (2016.02); *H01L 33/502* (2013.01)

(58) Field of Classification Search
CPC . C09K 11/025; C09K 11/0883; C09K 11/703; C09K 11/883; H01L 3/502
See application file for complete search history.

(56) References Cited

U.S. PATENT DOCUMENTS

| | | |
|---|---|---|
| 9,577,149 B2 | 2/2017 | Lu et al. |
| 10,676,666 B2* | 6/2020 | Kwon ............ H01L 33/502 |
| 2010/0009071 A1 | 1/2010 | Chopra et al. |
| 2015/0228866 A1* | 8/2015 | Daniels ............ C09K 11/703 |
| | | 252/301.36 |

FOREIGN PATENT DOCUMENTS

EP    2599898 A1    6/2013

OTHER PUBLICATIONS

Pradhan et al: Synthesis of High-Quality Metal Sulfide Nanoparticles from Alkyl Xanthate Single Precursors in Akylamine Solvents; J Phys. Chem B. vol. 107, No. 50. 2003, pp. 13843 -13854.*
International Search Report WO19072882A1—PCT/EP2018/077540 dated Nov. 30, 2018 (pp. 1-4).
Pradhan et al: Synthesis of High-Quality Metal Sulfide Nanoparticles from Alkyl Xanthate Single Precursors in Alkylamine Solvents; J. Phys. Chem. B, vol. 107, No. 50, 2003, pp. 13843-13854.
Dubois et al., A Versatile Strategy for Quantum Dot Ligand Exchange; JACS, vol. 129, 2007, pp. 482-483.
Jiazi Wang et al: "Diethyldithiocarbamate functionalized CdSe/CdS quantum dots as a fluorescent probe for copper ion detection", Spectrochimica Acta. Part A: Molecular and Biomolecular Spectroscopy, Elsevier, Amsterdam, NL, vol. 81, No. 1, May 30, 2011 (May 30, 2011), pp. 178-183, XP028291814, ISSN: 1386-1425, [retrieved on Jun. 12, 2011], DOI: 10.1016/J.SAA.2011.05.098.
Zhao et al., Dithiocarbamate Assembly on Gold; JACS, vol. 127, 2005, pp. 7328-7329.
Yanjie Zhang et al: "Dithiocarbamates as Capping Ligands for Water-Soluble Quantum Dots", ACS Applied Materials & Interfaces, vol. 2, No. 11, Nov. 24, 2010 (Nov. 24, 2010), pp. 3384-3395, XP055180671, ISSN: 1944-8244, DOI: 10.1021/am100996g.
Matthew T. Frederick et al: "Relaxation of Exciton Confinement in CdSe Quantum Dots by Modification with a Conjugated Dithiocarbamate Ligand", ACS NANO, vol. 4, No. 6, Jun. 22, 2010 (Jun. 22, 2010), US, pp. 3195-3200, XP055525192, ISSN: 1936-0851, DOI: 10.1021/nn1007435.
Bowles: The surface science of nanocrystals, Nature Materials 2016 (15) 141-153.
Rickey Seyler: Differential Scanning Calorimetry; Assignment of the Glass Transition, ASTM publication code No. PCN_04_012490_50 (2018) Copyright © 2003-2018 Polymer Science Learning Center l(pp. 1-7).
Onwudiwe: "Synthesis, Characterization and Thermal Studies of Zn(II), Cd(II) and Hg(II) Complexes of N-Methyl-N-Phenyldithiocarbamate: The Single Crystal Structure of [(C6H5)(CH3)NCS2]4Hg2" Int. J. Mol. Sci. 2011, 12, 1964-1978.

* cited by examiner

*Primary Examiner* — C Melissa Koslow
(74) *Attorney, Agent, or Firm* — Millen, White, Zelano & Branigan, P.C.; Harry B. Shubin

(57) ABSTRACT

Suggested is a semiconductor nano-sized light emitting material having a ligand.

10 Claims, No Drawings

SEMICONDUCTING LIGHT EMITTING MATERIAL

FIELD OF THE INVENTION

The present invention refers to the area of semiconductors and relate to new quantum dots with improved quantum yields, a process for obtaining them and further applications of the new semiconductors.

BACKGROUND ART

Quantum dots (QD) are semiconducting particles with diameters in the nano meter range (about 2 to 20 nm), which are so small that the optical and electronic properties of the crystals change. A special feature of the Quantum dots is that they change their colour with the particle diameter. In order to produce, for example, blue QDs, no other materials are required as for red QDs—they only have to be produced with different particle sizes. In addition to typical applications such as displays, QDs are now also used in many other areas, such as solar cells or processors.

Quantum dots can fluoresce and convert photons to other wavelengths as well as emit light. However, their outstanding characteristics are undoubtedly the ability to improve the background lighting in displays. LCD TVs use a white background light and then filter the blue, green and red light to display colours. Blue LEDs with a phosphor layer are usually used for this so-called "backlight". However, it is disadvantageous that the phosphor layer cannot completely convert blue light into white light.

With the help of Quantum Dots, this problem can be solved since they are capable of converting blue light exactly to the desired wavelength depending on their size. By means of more or fewer dots of a colour, the colour ratio can also be controlled so that the colour-generating LC layer has to correct less. The strongest technological advantage of QD backlight over phosphor based "white LED" backlight is the narrow FWHM (<50 nm) which enables wide colour gamut, e.g. increasing the amount of displayed colours.

The most important semiconductor materials, which are also suitable for the production of Quantum Dots, include cadmium compounds, especially CdS and CdSe. However, the disadvantage is that cadmium is highly toxic. A promising alternative would be InP, but here the quantum yield is not satisfactory. Therefore, the search is ongoing for specific new ligands improving quantum of QDs, particularly by reducing trap emission.

Metallic complexes of dithiocarbamates (M-DTC) and alkyl dithiocarbonates (so called xanthates) are widely used as single source precursors for shell growth providing elements of e.g. ZnS shell upon a core nanocrystal as reported for example in US 2015 0228866 A1 (NANOCO) or J. PHYS. CHEM. B, 107(50), pp 13843-13854 (2003). It should be mentioned that the zinc DTC salts are used as precursors for ZnS and were decomposed at elevated temperatures, while Cd xanthate is not mentioned as a ligand, but as a single source precursor for synthesis of Cd-based QDs.

It is also known from papers published by ZHAO ET AL [JACS 127, pp7328-7329, (2005)] and DUBOIS ET AL respectively [JACS 129, pp482-483 (2007)] that DTC and xanthate molecules are useful as QDs capping ligands. The documents, however, are silent with respect to specific metal complexes of these compounds and their ability to passivate traps when bound to the outer surface of a QD.

Notwithstanding the teaching of the prior art, it has been the object of the present invention providing new semiconductor light emitting materials with improved quantum yield.

DESCRIPTION OF THE INVENTION

A first object of the present invention is directed to a semiconductor nano-sized light emitting material comprising or consisting of a core, optionally one or more shell layers and a ligand coated onto the core or the outermost surface of the shell layers, wherein the ligand is at least one thio metal salt. Although the term "nano-sized" is clear for every skilled person working in the technological are to which the present invention belongs, it should be expressed that nano-sized has the meaning of an average particle diameter in the range of 0.1 nm to 999 nm, preferably 1 nm to 150 nm, more preferably 3 nm to 50 nm.

According to the present invention, the term "semiconductor" means a material that has electrical conductivity to a degree between that of a conductor (such as copper) and that of an insulator (such as glass) at room temperature. Preferably, a semiconductor is a material whose electrical conductivity increases with the temperature.

Thus, according to the present invention, semiconducting light emitting nanoparticle is taken to mean that the light emitting material which size is in between 0.1 nm and 999 nm, preferably 1 nm to 150 nm, more preferably 3 nm to 50 nm, having electrical conductivity to a degree between that of a conductor (such as copper) and that of an insulator (such as glass) at room temperature, preferably, a semiconductor is a material whose electrical conductivity increases with the temperature, and the size is in between 0.1 nm and 999 nm, preferably 0.5 nm to 150 nm, more preferably 1 nm to 50 nm.

According to the present invention, the term "size" means the average diameter of the longest axis of the semiconducting nano-sized light emitting particles.

The average diameter of the semiconducting nano-sized light emitting particles are calculated based on 100 semiconducting light emitting nanoparticles in a TEM image created by a Tecnai G2 Spirit Twin T-12 Transmission Electron Microscope.

In a preferred embodiment of the present invention, the semiconducting light emitting nanoparticle of the present invention is a quantum sized material.

According to the present invention, the term "quantum sized" means the size of the semiconducting material itself without ligands or another surface modification, which can show the quantum confinement effect, like described in, for example, ISBN: 978-3-662-44822-9.

Generally, it is said that the quantum sized materials can emit tunable, sharp and vivid colored light due to "quantum confinement" effect.

In some embodiments of the invention, the size of the overall structures of the quantum sized material, is from 1 nm to 50 nm, more preferably, it is from 1 nm to 30 nm, even more preferably, it is from 5 nm to 15 nm.

Surprisingly, it has been observed that deposition of metal bidentate ligands of thio metal salt type, which are capable of replacing native ligands and coordinating to both positive and negative atoms in quantum material's surface, passivate the traps on the surface of the particles, thus leading to a significant increase of up to 30% in quantum yields, improved QY stability and therefore overcome the drawbacks of the prior art. The effect can further be increased by subsequently illuminating these materials.

One surprisingly found advantage of the present invention, i.e. the improved QY stability, is due to the addition of at least one thio metal salt to QD solution. This leads to an increased stability of the QD and therefore to an improved QY stability. Therefore also the emission stability of the QD is improved, which leads to longer term stable emission of the QD. This is due to the fact, that the ligands according to the present invention bin stronger to the surface of the QD.

Another advantage is associated with the fact that hydrophilicity of the thio ligands can be tailored by changing the alkyl group in amines and/or alcohols that are used as precursors. For example, more polar groups may render the material also soluble in preferred more polar solvents such as PGMEA.

It should be noted that said ligands can be added to crude material, which means that they are incorporated into the last step of the QD synthesis, but is also possible to use commercial QDs for after ligand purification. The materials may have any possible shape, such as for example rods, dots, octahedrals, wires, tetrapods, platelets and the like.

Thio Metal Salts

Thio metal salts are salts which can be obtained according to general and procedures of organic chemistry known to any skilled person. For example, a general procedure for obtaining thiocarbamates and thiocarbonates is provided in J. MOL. SCIENCE, 12, pp 1964-1978 (2011) describing the manufacture by a nucleophilic substitution between primary and secondary amines and carbon disulfide in alkaline medium.

Preferably said thio metal salts follow formula (I)

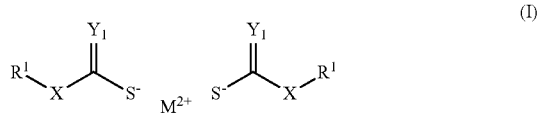
(I)

in which

M stands for a bivalent metal, preferably zinc, magnesium, copper or their mixtures;

X stands independently from each other for —O— or —S— or —$NR^2$—;

$Y^1$ stands independently from each other for —O— or —S—;

$R^1$, $R^2$ stand independently from each other for an alkyl, alkenyl, aryl and/or aralkyl chain having 2 to 25 carbon atoms optionally substituted by a functional group; or a group according to formula (II) and/or (III)

—(CHR$^5$)$_x$O(CHR$^5$)$_{y2}$—NR$^3$R$^4$ (II)

—(CH$_2$CHR$^5$O)$_z$R$^6$ (III)

wherein $R^3$, $R^4$ stand independently from each other linear or branched alkyl chains having 1 to 6 carbon atoms;

$R^5$ stands for hydrogen or methyl;

$R^6$ stands for an alkyl chain having 1 to 4 carbon atoms, optionally substituted by a functional group;

x, y2 stand independently from each other for integers of from 1 to 5; and z stands for an integer of from 1 to 30.

In a preferred embodiment according to the invention X stands independently from each other for —O— or —$NR^2$—. In another preferred embodiment according to the invention X stands for —O—. In another preferred embodiment according to the invention X stands for $NR^2$—. In one preferred embodiment according to the invention $Y^1$ stands for S.

The preferred ligands may have the general structures (structure I, II and III). The structures show Zn as the bivalent metal, but can be replaced by Mg or Cu or their mixtures:

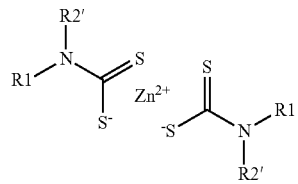

Structure I - Zinc dialkyl thiocarbamate

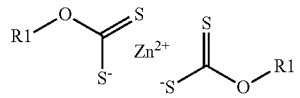

Structure II - Zinc alkyl dithiocarbamate (Xanthate)

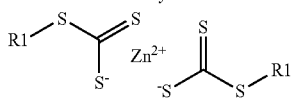

Structure III - Zinc alkyl trithiocarbamate

In a most preferred embodiment according to the invention M stands for Zn.

In some embodiments $R^1$ is similar to $R^2$ and in other structures the groups can be different. The $R^1$ and $R^2$ groups may be selected from any functional group, and are generally hydrocarbons having carbon atoms in the range of 2 to about 25, preferably between about 6 to about 20 carbon atoms, more preferably between about 7 to 20 carbon atoms and most preferably in the range of about 8 to about 18 carbon atoms. Examples include alkyl, alkenyl, alkynyl, aryl and aralkyl.

The present invention encompasses the teaching that chain length can affect the QY stability over time. For example, Zn(C18)DTC is stable compared to Zn(C2)DTC which shows QY drop 48 hours after illumination is stopped.

Commonly used suitable zinc-dithio-ligands include, but are not limited to zinc diethyldithiocarbamate, zinc dioctyldithiocarbamate, zinc dioctadecyldithiocarbamate, zinc oleylxanthate, and their mixtures.

According to some embodiments $R^1$ and $R^2$ (in structures I, II and III) can be functional groups with the ability to tailor the hydrophilicity of QDs to render it soluble in more polar solvents compared to toluene. An example of such an R (or R') group is a hydrocarbon chain with a carboxylic acid, amine, amide, ester, ether, hydroxyl or alkoxy functionality.

$R^1$ and $R^2$ can also be individually represented by formula (II)

—(CHR$^5$)$_x$O(CHR$^5$)$_{y2}$—NR$^3$R$^4$ (II)

wherein $R^3$, $R^4$ and $R^5$ stand independently from each other linear or branched alkyl chains having 1 to 6 and preferably 2 to 4 carbon atoms.

In the alternative $R^3$, $R^4$ and $R^5$ may represent an amphiphilic group such as PEG (polyethylene glycol) as for example formula (III)

—(CH$_2$CHR$^5$O)$_z$R$^6$ (III)

wherein z represents an integer of from 1 to about 30, preferably of from about 4 to about 25 and particularly from about 12 to about 18. The ethers may represent polyalkylene glycols or polypropylene glycols or their mixtures. In order to achieve high solubility in PGMEA and similar solvents a molecular weight of at most 1300 Da, preferably between about 350 and about 800 Dalton.

R⁶ stands for an alkyl chain having 1 to 4 carbon atoms, optionally substituted by a functional group, such as a tetrahydrofuryl group or an acyl group, particularly an acrylic acid residue.

A particularly preferred structure is presented by formula (IIIb):

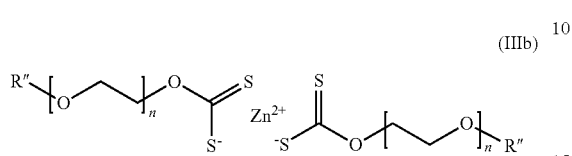

Particularly preferred ligands are metal thiocarbamates and/or metal thiocarbonates.

Particularly preferred ligands are represented by the following structures:

Zn(C2)DTC:

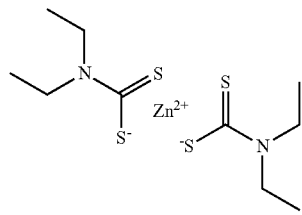

Zn(C18)DTC:

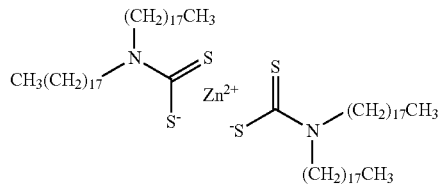

Zn(C18)Xanthate:

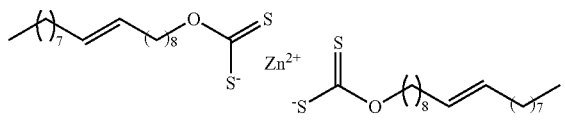

It should be noted that the presence of a bivalent metal, is crucial for the invention. Note that in the absence of such metals the thio metal salts exhibit rather low quantum yields. In a preferred embodiment according to the invention the bivalent metal is zinc.

The preferred ligands represent dialkyl thiocarbamates and/or a dialkyl dithiocarbonates, representing so-called Z-type ligands as defined in NATURE MATERIALS 15, pp141-153 (2016).

Further disclosed herein is a compound of Formula (I)

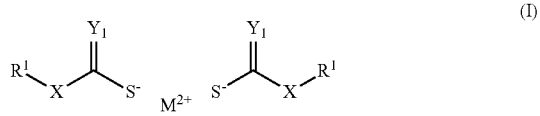

in which

M stands for a bivalent metal, preferably zinc, magnesium, copper or their mixtures;

X stands for —O— or —S— or —NR²—;

Y¹ stands independently from each other for —O— or —S—;

R¹, R² stand independently from each other for an alkyl, alkenyl, alkenyl, aryl and/or aralkyl chain having 7 to 20 carbon atoms, optionally substituted by a functional group; or a group according to formula (II) and/or (III)

—(CHR⁵)ₓO(CHR⁵)ᵧ₂—NR³R⁴     (II)

—CH₂CHR⁵O)ᵤR⁶     (III)

R³, R⁴ stand independently from each other linear or branched alkyl chains having 1 to 6 carbon atoms;

R⁵ stands for hydrogen or methyl;

R⁶ stands for an alkyl chain having 1 to 4 carbon atoms, optionally substituted by a functional group;

x, y2 stand independently from each other for integers of from 1 to 5; and z stands for an integer of from 1 to 30.

In a preferred embodiment according to the invention M stands for Zn. In a further preferred embodiment according to the invention R¹, R² stand independently from each other for an alkyl, alkenyl, alkenyl, aryl and/or aralkyl chain having 7 to 25 carbon atoms, more preferred from 10 to 22 carbon atoms, further more preferred from 12 to 18 carbon atoms and most preferred 18 carbon atoms, optionally substituted by a functional group. In a further preferred embodiment according to the invention Y¹ stands for S. In a further preferred embodiment according to the invention X stands independently from each other for —O— or —NR²—. In another preferred embodiment according to the invention X stands for —O—. In another preferred embodiment according to the invention X stands for NR²—.

Semiconductor Materials

Suitable semiconductor materials forming the core or the core/shell body of the material according to the present invention may represent single compounds or mixtures of two, three or even more of them.

In a first preferred embodiment of the present invention said core is formed from one, two or more compounds according to formula (IV), $$[A^1B^1] \quad (IV)$$

in which

[A¹] stands for a metal selected from the group consisting of zinc, cadmium, indium or their mixtures;

[B¹] stands for a non-metal selected form the group consisting of sulphur, selenium, phosphor or their mixtures.

More preferably [A¹B¹] stands for one, two or more compounds selected from the group consisting of CdS, CdSe, CdSeS, CdZnS, ZnS, ZnSe, ZnSeS, and InP.

According to the present invention, a type of shape of the core of the semiconducting light emitting nanoparticle, and shape of the semiconducting light emitting nanoparticle to be synthesized are not particularly limited.

For examples, spherical shaped, elongated shaped, star shaped, polyhedron shaped, pyramidal shaped, tetrapod shaped, tetrahedron shaped, platelet shaped, cone shaped, and irregular shaped core and—or a semiconducting light emitting nanoparticle can be synthesized.

In some embodiments of the present invention, the average diameter of the core is in the range from 1.5 nm to 3.5 nm.

In another preferred embodiment of the present invention said shell or said shells are formed from one, two or more compounds according to formula (V), $$[A^2B^2] \quad (V)$$

in which

[$A^2$] stands for a metal selected from the group consisting of zinc, cadmium or their mixtures;

[$B^2$] stands for a non-metal selected form the group consisting of sulphur, selenium, tellurium or their mixtures.

Preferably [$A^2B^2$] stands for one, two or more compounds selected from the group consisting of CdS, CdSe, CdSeS, CdZnS, ZnS, ZnSe, ZnTe, ZnTeSeS and ZnSeS.

Overall preferred are materials comprising a core [$A^1B^1$] and at least one shell, [$A^2B^2$], preferably said core [$A^1B^1$] and the shell [$A^2B^2$] forms core/shell structure, more preferably said core/shell structure [$A^1B^1$]/[$A^2B^2$] being selected from the group consisting of CdSeS/CdZnS, CdSeS/CdS, ZnS CdSe/ZnS, InP/ZnS, InP/ZnSe, InP(Zn)/ZnSe, ZnSe/CdS, ZnSe/ZnS, or their mixtures. In another preferred embodiment of the present invention the materials are free of cadmium.

In some embodiments of the present invention, the semiconducting light emitting nanoparticle further comprises a 2nd shell layer onto said shell layer, preferably the 2nd shell layer comprises or a consisting of a 3rd element of group 12 of the periodic table and a 4th element of group 16 of the periodic table, more preferably the 3rd element is Zn, and the 4th element is S, Se, or Te with the proviso that the 4th element and the 2nd element are not the same.

In a preferred embodiment of the present invention, the 2nd shell layer is represented by following formula (VI), $$ZnS_xSe_yTe_z\text{-} \qquad (VI)$$

wherein, $0 \le x \le 1$, $0 \le y \le 1$, $0 \le z \le 1$, and $x+y+z=1$, preferably, the shell layer is ZnSe, $ZnS_xSe_y$, $ZnSe_yTe_z$, or $ZnS_xTe_z$ with the proviso that the shell layer and the 2nd shell layer is not the same.

In some embodiments of the present invention, said 2nd shell layer can be an alloyed shell layer or a graded shell layer, preferably said graded shell layer is, $ZnS_xSe_y$, $ZnSe_yTe_z$, or $ZnS_xTe_z$, more preferably it is $ZnS_xSe_y$.

In some embodiments of the present invention, the semiconducting light emitting nanoparticle can further comprise one or more additional shell layers onto the 2nd shell layer as a multishell.

According to the present invention, the term "multishells" stands for the stacked shell layers consisting of three or more shell layers.

For example, CdSe/CdS, CdSeS/CdZnS, CdSeS/CdS/ZnS, ZnSe/CdS, CdSe/ZnS, InP/ZnS, InP/ZnSe, InP/ZnSe/ZnS, InZnP/ZnS, InZnP/ZnSe, InZnP/ZnSe/ZnS, InGaP/ZnS, InGaP/ZnSe, InGaP/ZnSe/ZnS, InZnPS/ZnS, InZnPS/ZnSe, InZnPS/ZnSe/ZnS, ZnSe/CdS, ZnSe/ZnS or combination of any of these, can be used. Preferably, InP/ZnS, InP/ZnSe, InP/ZnSe$_x$S$_{1-x}$, InP/ZnSe$_x$S$_{1-x}$/ZnS, InP/ZnSe/ZnS, InZnP/ZnS, InP/ZnSe$_x$Te$_{1-x}$/ZnS, InP/ZnSe$_x$Te$_{1-x}$, InZnP/ZnSe, InZnP/ZnSe/ZnS, InGaP/ZnS, InGaP/ZnSe, InGaP/ZnSe/ZnS.

In some embodiments of the present invention, the volume ratio between the shell and the core of the semiconducting light emitting nanoparticle is 5 or more, preferably, it is in the range from 5 to 40, more preferably it is from to 30.

According to the present invention, said shell/core ratio is calculated using following formula (VII).

wherein the symbols have the following meaning

Vshell=the volume of shell layer(s),

Vcore=the volume of core,

Mw (Total shell elements)=molecular weight of total shell elements,

Mw (Total core elements)=molecular weight of total core elements

ρ (Total shell elements)=density of total shell elements

ρ (Total core elements)=density of total core elements

Manufacturing Process

Another object of the present invention is directed to a process for manufacturing a semiconductor nano-sized light emitting material comprising or consisting of a core, optionally one or more shell layers and a ligand coated onto the core or the outermost surface of the shell layers Therefore, the present invention includes two alternative embodiments for the materials: the first is a structure consisting of a [$A^1B^1$] as a single core on which the ligand is deposited and the second is a structure consisting of a core [$A^1B^1$] and at least one shell [$A^2B^2$], preferably two or more shells [$A^2B^2$]$^2$ ... [$A^xB^x$]$^x$. In case the materials consist of a core and at least one shell, core material [$A^1B^1$] and [$A^2B^2$] are different, for example InP as the core and ZnSe forming a shell. In case there are more shells, the materials may be still different, however it also possible that core and for example the outer shell are identical.

As far as the nature of the compounds showing an [AB] structure and the preferred single or multiple structures are concerned reference is made to the explanations infra which apply also with regard to the process.

Therefore, a preferred embodiment of the present invention is a process wherein step (a) and/or step (b) encompasses providing salts of two different metals [$A^1$] or [$A^2$] and/or adding sources of two different non-metals [$B^1$] or [$B^1$] respectively. In case all raw materials are added at the same time a core consisting of all these compounds is formed. However, it is particularly preferred forming the core first and subsequently adding those components designated to form a shell around said core. This can be done stepwise to build up complex particles with a core and two or more shells.

For example, suitable salts of metal [A1] or [$A^2$] encompass halides, particularly chlorides or iodides, or carboxylates, such as for example acetates or oleates. Suitable sources of non-metals [$B^1$] or [$B^1$] comprise for example complexes with phosphine.

The molar ratio of these components [A] and [B] can differ in wide ranges, however it is preferred to apply molar ratios in the range of about 4:1 to 1:4. In another embodiment the molar ratios are about 1:1. Reaction usually takes place in the presence of a solvent, for example a high-boiling amine like oleyl amine. Once the components to form the core are brought into contact they were kept under reflux at a temperature of about 150 to about 200° C.

Subsequently the remaining components designated to form the shell are introduced and temperature increased stepwise up to 350° C., preferably 200 to 320° C. The complete reaction requires up to 5 hours.

Once reaction is completed the intermediate semiconductor material [AB]—either consisting of a single core or showing a core-shell(s) structure is purified by washing and centrifugation using polar and non-polar solvents.

Subsequently the nanocrystals are dissolved or at least dispersed in an organic solvent (e.g. toluene) and treated with a solution of a thio metal salt as defined in detail above. In a preferred embodiment according to the invention the nanocrystals are dissolved or at least dispersed in an organic solvent (e.g. toluene) and treated with a solution of a metal thiocarbamate and/or thiocarbonate.

The thio metal salts are deposited on the surface of the intermediate compound $[A^1B^1]$ or $[A^1B^1]/[A^2B^2]$ in an amount of from about 2 to about 98 wt. %, more preferably from about 3 to about 50 wt. % and even more preferably from about 5 to about 25 wt. %, which may depend on the molar mass of the ligand. In a preferred embodiment according to the invention the metal thiocarbamates and/or thiocarbonates are deposited on the surface of the intermediate compound $[A^1B^1]$ or $[A^1B^1]/[A^2B^2]$ in an amount of from about 2 to about 98 wt. %, more preferably from about 3 to about 50 wt.-% and even more preferably from about 5 to about 25 wt.-%, which may depend on the molar mass of the ligand.

A critical step for increasing quantum yield of nano-sized material is illumination using blue light. Preferred peak light wavelengths range from about 300 to about 650 nm and particularly from about 365 about 470 nm. In another preferred embodiment light intensities range from about 0.025 to about 1 $Wcm^{-2}$, more preferably from about 0.05 to about 0.5 Wcm-2

Matrix Composition

Another object of the present invention refers to a composition comprising at least one semiconductor nano-sized light emitting material as explained above and at least one additional material, preferably the additional material is selected from the group consisting of organic light emitting materials, inorganic light emitting materials, charge transporting materials, scattering particles, and matrix materials, preferably the matrix materials are optically transparent polymers.

According to the present invention, a wide variety of publically known matrix materials suitable for optical devices can be used preferably. In a preferred embodiment according to the invention the matrix material is transparent. According to the present invention, the term "transparent" means at least around 60% of incident light transmit at the thickness used in an optical medium and at a wavelength or a range of wavelength used during operation of an optical medium. Preferably, it is over 70%, more preferably, over 75%, the most preferably, it is over 80%.

In some embodiments of the present invention, the transparent matrix material can be a transparent polymer.

According to the present invention the term "polymer" means a material having a repeating unit and having the weight average molecular weight (Mw) 1000 or more.

The molecular weight $M_w$ is determined by means of GPC(=gel permeation chromatography) against an internal polystyrene standard.

In some embodiments of the present invention, the glass transition temperature (Tg) of the transparent polymer is 70° C. or more and 250° C. or less.

Tg can be measured based on changes in the heat capacity observed in Differential scanning colorimetry like described in http://pslc.ws/macrog/dsc.htm, Rickey J Seyler, Assignment of the Glass Transition, ASTM publication code number (PCN) 04-012490-50.

For examples, as the transparent polymer for the transparent matrix material, poly(meth)acrylates, epoxides, polyurethanes, polysiloxanes, can be used preferably.

In a preferred embodiment of the present invention, the weight average molecular weight (Mw) of the polymer as the transparent matrix material is in the range from 1,000 to 300,000. More preferably it is from 10,000 to 250,000.

Solvent Formulation

Another object of the present invention covers a formulation comprising the composition as explained above and at least one solvent. These kinds of formulations are of interest in case the material is designated for coating on a specific surface.

Suitable solvents can be selected from the group consisting of purified water; ethylene glycol monoalkyl ethers, such as, ethylene glycol monomethyl ether, ethylene glycol monoethyl ether, ethylene glycol monopropyl ether, and ethylene glycol monobutyl ether; diethylene glycol dialkyl ethers, such as, diethylene glycol dimethyl ether, diethylene glycol diethyl ether, diethylene glycol dipropyl ether, and diethylene glycol dibutyl ether; ethylene glycol alkyl ether acetates, such as, methyl cellosolve acetate and ethyl cellosolve acetate; propylene glycol alkyl ether acetates, such as, propylene glycol monomethyl ether acetate (PGMEA), propylene glycol monoethyl ether acetate, and propylene glycol monopropyl ether acetate; ketones, such as, methyl ethyl ketone, acetone, methyl amyl ketone, methyl isobutyl ketone, and cyclohexanone; alcohols, such as, ethanol, propanol, butanol, hexanol, cyclo hexanol, ethylene glycol, and glycerin; esters, such as, ethyl 3-ethoxypropionate, methyl 3-methoxypropionate and ethyl lactate; and cyclic asters, such as, γ-butyro-lactone; chlorinated hydrocarbons, such as chloroform, dichloromethane, chlorobenzene, dichlorobenzene.

Also preferred are solvents selected from one or more members of the group consisting of aromatic, halogenated and aliphatic hydrocarbons solvents, more preferably selected from one or more members of the group consisting of toluene, xylene, ethers, tetrahydrofuran, chloroform, dichloromethane and heptane.

Those solvents are used singly or in combination of two or more, and the amount thereof depends on the coating method and the thickness of the coating.

More preferably, propylene glycol alkyl ether acetates, such as, propylene glycol monomethyl ether acetate (hereafter "PGMEA"), propylene glycol monoethyl ether acetate, propylene glycol monopropyl ether acetate, purified water or alcohols can be used.

Even more preferably, purified water can be used.

The amount of the solvent in the formulation can be freely controlled according to further treatments. For example, if the formulation is designated to be spray-coated, it can contain the solvent in an amount of 90 wt. % or more. Further, if a slit-coating method, which is often adopted in coating a large substrate, is to be carried out, the content of the solvent is normally 60 wt. % or more, preferably 70 wt. % or more.

Devices

The present invention is also directed to the use of the semiconductor nano-sized light emitting material of the present invention in an electronic device, optical device or in a biomedical device as for example In some embodiments of the present invention, the optical device can be a liquid crystal display, Organic Light Emitting Diode (OLED), backlight unit for display, Light Emitting Diode (LED), Micro Electro Mechanical Systems (here in after "MEMS"), electro wetting display, or an electrophoretic display, a lighting device, and/or a solar cell.

The present invention also covers an optical medium comprising the semiconductor nano-sized light emitting material, the composition or the formulation each of them as explained above.

Finally, the present invention also refers to an optical device comprising said optical medium as explained above.

Further Embodiments

Embodiment 1: A semiconductor nano-sized light emitting material comprising or consisting of a core, optionally one or more shell layers and a ligand coated onto the core or the outermost surface of the shell layers, wherein the ligand is at least one thio metal salt.

Embodiment 2: The material of embodiment 1, wherein said ligand is represented by formula (I)

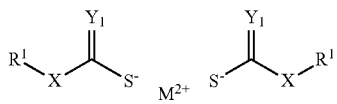

in which
M stands for a bivalent metal, preferably zinc, magnesium, copper or their mixtures;
X stands for —O— or —S— or —NR$^2$—;
Y$^1$ stands for —O— or —S—;
R$^1$, R$^2$ stand independently from each other for an alkyl, alkenyl, aryl and/or aralkyl chain having 2 to 25 carbon atoms, optionally substituted by a functional group; or
a group according to formula (II) and/or (III)

—(CHR$^5$)$_x$O(CHR$^5$)$_{y2}$—NR$^3$R$^4$ (II)

—CH$_2$CHR$^5$O)$_z$R$^6$ (III)

R$^3$, R$^4$ stand independently from each other linear or branched alkyl chains having 1 to 6 carbon atoms;
R$^5$ stands for hydrogen or methyl;
R$^6$ stands for an alkyl chain having 1 to 4 carbon atoms, optionally substituted by a functional group;
x, y2 stand independently from each other for integers of from 1 to 5; and
stands for an integer of from 1 to 30.

Embodiment 3: The material according to embodiment 1 or 2, wherein said ligand is represented by formula (I) and wherein R$^1$, R$^2$ stand independently from each other for an alkyl, alkenyl, aryl and/or aralkyl chain having 7 to 20 carbon atoms, optionally substituted by a functional group.

Embodiment 4: The material according to any one of embodiments 1 to 3, wherein the ligand is a metal dialkyl thiocarbamate and/or a metal dialkyl dithiocarbonate and/or a metal alkyl trithiocarbamate.

Embodiment 5: The material according to any one of embodiments 1 to 4, wherein said core is formed from one, two or more compounds according to formula (IV)

[A$^1$B$^1$] (IV)

in which
[A$^1$] stands for a metal selected from the group consisting of zinc, cadmium, indium or their mixtures;
[B$^1$] stands for a non-metal selected form the group consisting of sulphur, selenium, phosphor or their mixtures.

Embodiment 6: The material of embodiment 5, wherein [A$^1$B$^1$] stands for one, two or more compounds selected from the group consisting of CdS, CdSe, CdSeS, CdZnS, ZnS, ZnSe, ZnSeS, and InP.

Embodiment 7: The material according to any one of embodiments 1 to 6, wherein said shell or said shells are formed from one, two or more compounds according to formula (V),

[A$^2$B$^2$] (V) in which [A$^2$] stands for a metal selected from the group consisting of zinc, cadmium or their mixtures; [B$^2$] stands for a non-metal selected form the group consisting of sulphur, selenium, tellurium or their mixtures.

Embodiment 8: The material of embodiment 7, wherein [A$^2$B$^2$] stands for one, two or more compounds selected from the group consisting of CdS, CdSe, CdSeS, CdZnS, ZnS, ZnSe and ZnSeS, ZnSeSTe.

Embodiment 9: The material according to any one of embodiments 1 to 8, wherein the material comprises a core [A$^1$B$^1$] and at least one shell [A$^2$B$^2$], and said [A$^1$B$^1$]/[A$^2$B$^2$] being selected from the group consisting of CdSeS/CdZnS, CdSe/ZnS, InP/ZnS, InP/ZnSe, InP(Zn)/ZnSe, ZnSe/CdS, ZnSe/ZnS or their mixtures.

Embodiment 10: A semiconductor nano-sized light emitting material comprising or consisting of a core, optionally one or more shell layers and a ligand coated onto the core or the outermost surface of the shell layers, obtainable or obtained by the following steps:

Embodiment 12: A composition comprising at least one semiconductor nano-sized light emitting material according to any one of embodiments 1 to 10, and at least one additional transparent matrix material.

Embodiment 13: A formulation comprising at least one semiconductor nano-sized light emitting material according to any one of embodiments 1 to or the composition of embodiment 12, and at least one solvent.

Embodiment 14: The use of the semiconductor nano-sized light emitting material according to any one of embodiments 1 to 10, the composition of embodiment 12, or the formulation of embodiment 13 in an electronic device, optical device or in a biomedical device.

Embodiment 15: An optical medium comprising the semiconductor nano-sized light emitting material according to any one of embodiments 1 or 10, the composition of embodiment 12 or the formulation of embodiment 13.

Embodiment 16: An optical device comprising said optical medium according to embodiment 15.

Embodiment 17: A compound of Formula (I)

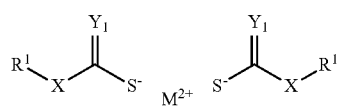

in which
M stands for a bivalent metal, preferably zinc, magnesium, copper or their mixtures;
X stands for —O— or —S— or —NR$^2$—;
Y$^1$ stands for —O— or —S—;
R$^1$, R$^2$ stand independently from each other for an alkyl, alkenyl, aryl and/or aralkyl chain having 7 to 25 carbon atoms, optionally substituted by a functional group; or
a group according to formula (II) and/or (III)

—(CHR$^5$)$_x$O(CHR$^5$)$_{y2}$—NR$^3$R$^4$ (II)

—CH$_2$CHR$^5$O)$_z$R$^6$ (III)

R$^3$, R$^4$ stand independently from each other linear or branched alkyl chains having 1 to 6 carbon atoms;
R$^5$ stands for hydrogen or methyl;
R$^6$ stands for an alkyl chain having 1 to 4 carbon atoms, optionally substituted by a functional group;
x, y2 stand independently from each other for integers of from 1 to 5; and
z stands for an integer of from 1 to 30.

WORKING EXAMPLES

Several semiconductors are prepared and subjected to surface treatment. Subsequently they are irradiated to enhance/improve quantum yields.

For illumination, a lighting setup built with Philips Fortimo 3000 lm 34W 4000K LED downlight module (phosphor disc removed). A 1.9 nm thick Perspex pane® is placed on its top. The distance between the LEDs and the Perspex pane® is 31.2 mm. The 20 ml sealed sample vials is placed on the Perspex pane® inside a plastic cylinder (diameter 68 mm, height 100 mm). A photo enhancement system with sealed sample vials inside the cylinder is used. The vials with the solution of QDs are placed on the Perspex and illuminated from below. Optionally, to prevent the solution from extensive heating and evaporation of the solvent, the vials are placed in the water bath. The peak wavelength of the illumination is 455 nm. The irradiance at 450 nm is measured by an Ophir Nova II® and PD300-UV photodetector and measured to be 300 mW/cm$^2$.

Example 1

Synthesis of InP/ZnSe 112 mg of InI$_3$, and 150 mg ZnCl$_2$ are dissolved in 2.5 mL oleylamine. At 180° C. 0.22 mL of hexaethylphosphorous triamide (DEA)3P) is added to the solution and is kept at this temperature for 20 min. After 20 min, 0.55 mL of anion shell precursor (2M TOP:Se) is added slowly in the solution. The solution is then heated stepwise, followed by successive injections of cation (2.4 mL of 0.4M Zn-acetate in oleylamine) and anion (0.38 mL of 2M TOP:Se) shell precursor at temperatures between 200° C. and 320° C.

Example 2

Synthesis of Zn-dioctadecyldithiocarbamate (Zn(C18)DTC)

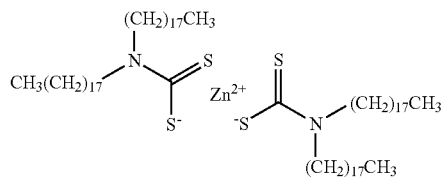

Into 100 mL round bottom flask equipped with Claisen adapter, magnetic stirrer and equalizing pressure dropping funnel, dioctadecylamine (>99% from Sigma-Aldrich, 4.8 mmol) is placed. Then carbon disulfide (anhydrous, ≥99% from Sigma-Aldrich, 9.6 mmol, 2 Equivalents) is added to dissolve the amine completely. NaOH (4.9 mmol, 1.0 Equivalents) are dissolved at room temperature (20° C.) with deionized water. After addition of NaOH solution, the colour changed to yellow. The reaction is allowed to stir for two days under ambient atmosphere until all the CS$_2$ evaporated and precipitate (dioctadecyl dithiocarbamate sodium salt) is formed. The work-up process includes vacuum filtration by Buchner.

Subsequently the dithiocarbamate thus obtained is reacted with Zinc chloride to form a zinc complex. Into 150 mL round bottom flask equipped with Claisen adapter, magnetic stirrer and equalizing pressure dropping funnel, dioctadecylamine sodium salt (1.5 mmol) dissolve at room temperature in ethanol: chloroform 1:1 is placed. In the next step ZnCl$_2$ (0.9 mmol, 0.61 Equivalents) is dissolved at room temperature in an ethanol:chloroform 1:1 mixture, placed into the equalizing pressure dropping funnel and added dropwise for 15 minutes. Precipitate is formed after one day. Additional stirring of the mixture is allowed for 72 hours at 20° C., and then work-up using a vacuum filtration by Buchner is conducted. The white yellow solid dries over Buchner funnel for 2 hours under vacuum.

Example 3

Synthesis of Zn-oleyl xanthate

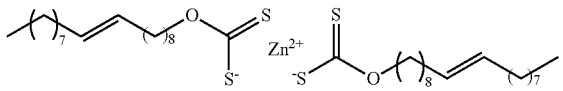

Into 50 mL Erlenmeyer, KOH and oleyl alcohol (85% grade, Sigma-Aldrich) are placed and reacted at 20° C. for 4 hours. After partially dissolving of KOH, the turbid solution is decanted (using the liquor) into 3-neck round bottom flask (3-rbf) equipped with magnetic stirrer and reflux condenser (only for protection) and equalizing pressure dropping funnel. Carbon disulfide dissolved in diethyl ether (12 mL) is placed into the equalizing pressure dropping funnel and added dropwise for 30 minutes. During the addition, pale yellow solid is formed. The reaction is allowed to stir 10 hours at 20° C. under dark conditions until most of the moisture is vanished. During stirring, most of the crude becomes solid. The work-up process included vacuum filtration by Buchner or drying by vacuum. Trituration is done with diethyl ether to obtain pure oleyl xanthate potassium salt.

Subsequently the xanthate thus obtained is reacted with Zinc chloride to form a zinc complex. Into 100 mL round bottom flask equipped Claisen adapter, magnetic stirrer and equalizing pressure dropping funnel, oleyl xanthate potassium salt (3.4 mmol) dissolve at room temperature (r.t) in THF is placed. In the next step ZnCl$_2$ (2.1 mmol, 0.61 Equivalents) dissolved at room temperature in THF is placed into the equalizing pressure dropping funnel and added dropwise for 10 minutes. Precipitate of white solid is formed after 24 hours. Additional stirring of the mixture is allowed for 2 days at 20° C., and then the product is worked-up using a vacuum filtration by Buchner. The white solid is rinsed 3 times with deionized water and then dried over vacuum.

Example 4

Purification of Quantum Material from Example 1

1 mL of the sample from EXAMPLE 1 is purified from excess ligands using toluene and ethanol as solvent and anti-solvent respectively followed by centrifugation and drying. The cleaning is repeated twice. The amount of organic ligands is calculated using thermal gravimetric analysis (TGA) (model TGA2, Metler Toledo). TG analysis shows 14% wt. of organic content.

30 mg of the quantum materials is dissolved in 1 mL toluene. Quantum yield (QY) is measured using Hamamatsu absolute quantum yield spectrometer (model: Quantaurus C11347). The solution is illuminated for 24 hours under blue led (300 mW/cm$^2$). The quantum yield of the illuminated sample is measured right after the illumination has stopped and 2 days after stopping the illumination.

Example 5

Surface Treatment with Zn-diethyl dithiocarbamate (Zn(C2)DTC)

0.027 mmol Zn(C2)DTC

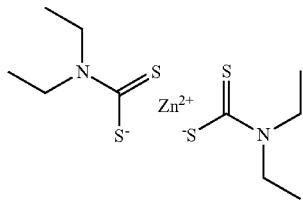

(97%, 329703-25G from Sigma-Aldrich) are dissolved in 0.5 mL toluene. Sonication (10 minutes) is applied to accelerate dissolving of Zn(C2)DTC in toluene. The solution is combined with 1 mL of the purified QDs solution (see EXAMPLE 4). Sonication is applied over about 20 minutes until a clear solution is obtained.

Example 6

Illumination of QM Treated with Zn-diethyl dithiocarbamate (Zn(C2)DTC)

The solution from (EXAMPLE 5) is placed under illumination for 24 hours under blue led (300 mW/cm$^2$). After 24 hours, the quantum yield of the sample is measured using Hamamatsu absolute quantum yield spectrometer (model: Quantaurus C11347). The quantum yield of the illuminated sample is measured right after the illumination has stopped and 2 days after stopping the illumination.

Example 7

Surface Treatment with Zn-dioctadecyl thiocarbamate (Zn(C18)DTC)

0.027 mmol Zn(C18)DTC (from EXAMPLE 2) are dissolved in 0.5 mL toluene. Sonication (10 minutes) is applied to accelerate dissolving of Zn(C18)DTC in toluene. The solution is combined with 1 mL of the purified QDs solution (see EXAMPLE 4). Sonication is applied over about 20 minutes until a clear solution is obtained.

Example 8

Illumination of QM Treated with Zn(C18)DTC

A solution described in (EXAMPLE 7) is placed under illumination for 24 hours under blue led (300 mW/cm$^2$). After 24 hours, the quantum yield of the sample is measured using Hamamatsu absolute quantum yield spectrometer (model: Quantaurus C11347). The quantum yield of the illuminated sample is measured right after the illumination has stopped and 2 days after stopping the illumination.

Example 9

Surface treatment with Dioctadecyl dithiocarbamate (C18DTC) 0.027 mmol C18DTC (prepared as described in EXAMPLE 2) are dissolved in 0.5 mL toluene. Sonication (10 minutes) is applied to accelerate dissolving of C18DTC in toluene. The solution is combined with 1 mL of the purified QDs solution (see EXAMPLE 4). Sonication is applied over about 20 minutes until a clear solution is obtained.

Example 10

Surface Treatment with Zn-oleyl xanthate (Zn(C18)xanthate)

0.027 mmol Zn(C18)xanthate (prepared as described in EXAMPLE 3) are dissolved in 0.5 mL toluene. Sonication (10 minutes) is applied to accelerate dissolving of Zn(C18) xanthate in toluene. The solution is combined with 1 mL of the purified QDs solution (see EXAMPLE 4). Sonication is applied over about 20 minutes until a clear solution is obtained.

Example 11

Illumination of QM Treated with Zn(C18)xanthate

A solution described in (EXAMPLE 10) is placed under illumination for 24 hours under blue led (300 mW/cm$^2$). After 24 hours the quantum yield of samples is measured using Hamamatsu absolute quantum yield spectrometer (model: Quantaurus C11347). The quantum yield of the illuminated sample is measured right after the illumination has stopped and 2 days after stopping the illumination.

The experimental results are presented in the following Tables 1 and 2 providing quantum yields and stability of Quantum yields of the samples.

TABLE 1

Quantum yield for Zn-dialkyl-DTC treated samples

| Samples | QY (%) |
|---|---|
| EXAMPLE 4 before illumination | 21 |
| EXAMPLE 4 after illumination | 40 |
| EXAMPLE 5 | 33 |
| EXAMPLE 6 | 53 |
| EXAMPLE 7 | 33 |
| EXAMPLE 8 | 61 |
| EXAMPLE 9 | 0.4 |
| EXAMPLE 10 | 33 |
| EXAMPLE 11 | 39 |

The EXAMPLES clearly indicate that the presence of a metal cation, here zinc, is crucial. EXAMPLE 5 for Zn(C18) DTC QY is 33% (before illumination), and only 0.4% for C18DTC (EXAMPLE 9). Moreover, Illumination can enhance QY significantly, and QY can significantly be increased when using Zn(C18)DTC.

TABLE 2

Stability of QY of the QM treated with different Zn-dialkylDTC (and xanthate), 48 hours after stopping illumination

| Samples | QY measure 2 days after stopping illumination (%) |
|---|---|
| EXAMPLE 4 | 21 |
| EXAMPLE 6 | 21 |

TABLE 2-continued

Stability of QY of the QM treated with different Zn-dialkylDTC
(and xanthate), 48 hours after stopping illumination

| Samples | QY measure 2 days after stopping illumination (%) |
|---|---|
| EXAMPLE 8 | 59 |
| EXAMPLE 11 | 41 |

The EXAMPLES clearly indicate that QY of InP/ZnSe (purified sample without external ligands) is not stable after stopping illumination and drops from 40% to 21%. InP/ZnSe with Zn(C2)DTC is also not stable. However, zinc dithio ligands with chain length of C18 (EXAMPLES 8 and 11) are stable and no drop in QY is observed.

Example 12

Synthesis and Purification of InP/ZnSe Quantum Dots 112 mg of $InI_3$, and 150 mg $ZnCl_2$ are dissolved in 2.5 mL oleylamine. At 180° C. 0.22 mL of hexaethylphosphorous triamide (DEA)3P) is added to the solution and is kept at this temperature for 20 min. After 20 min, 0.55 mL of anion shell precursor (2M TOP:Se) is added slowly in the solution. The solution is then heated stepwise, followed by successive injections of cation (2.4 mL of 0.4M Zn-acetate in oleylamine) and anion (0.38 mL of 2M TOP:Se) shell precursor at temperatures between 200° C. and 320° C., to obtain crude InP/ZnSe. 1 mL of the crude QDs is purified from excess ligands using toluene and ethanol as solvent and anti-solvent respectively followed by centrifugation and drying. The cleaning is repeated twice. The amount of organic ligands is calculated using thermal gravimetric analysis (TGA) (model TGA2, Metler Toledo). TG analysis shows 15% wt. of organic content.

Example 13

Stability Test by Dilution of QDs (from EXAMPLE 12)

25 mg of QDs from EXAMPLE 12 are dissolved in 1 ml toluene (anhydrous grade). The solution is kept under inert atmosphere (Argon). This solution is further diluted to a final concentration of 0.3 mg/ml. The QY is measured right after the dilution and after 24 hours of storage under ambient conditions.

Example 14

Stability Test by Dilution of QDs (from EXAMPLE 12) after Surface Treatment with Zinc Oleylxanthate 25 mg of QDs (from EXAMPLE 12) are dissolved in 1 mL toluene (anhydrous grade). The solution is kept under inert atmosphere (Argon). ZnC18Xanthate (prepared as described in EXAMPLE 3) (10 mg) is added to the QDs solution and the mixture is stirred for 16 hours. This solution is further diluted to a final concentration of 0.3 mg/ml. The QY is measured right after the dilution and after 24 hours of storage under ambient conditions.

Example 15

Stability Test by Dilution of InP/ZnS QDs (Red Emitting QDs Manufactured as Described in WO2014/162206 A1 and/or U.S. Pat. No. 9,343,301 BB)

25 mg of InP/ZnS (red emitting QDs manufactured as described in WO2014/162206 A1 and/or U.S. Pat. No. 9,343,301 BB) are dissolved in 1 ml toluene (anhydrous grade). The solution is kept under inert atmosphere (Argon). This solution is further diluted to a final concentration of 0.3 mg/ml. The QY is measured right after the dilution and after 24 hours of storage under ambient conditions.

Example 16

Stability Test by Dilution of InP/ZnS QDs (Red Emitting QDs Manufactured as Described in WO2014/162206 A1 and/or U.S. Pat. No. 9,343,301 BB) after Surface Treatment with Zn(C18)Xanthate 25 mg of InP/ZnS (red emitting QDs manufactured as described in WO2014/162206 A1 and/or U.S. Pat. No. 9,343,301 BB) are dissolved in 1 mL toluene (anhydrous grade). The solution is kept under inert atmosphere (Argon). Zn(C18)xanthate (10 mg) (prepared as described in EXAMPLE 3) is added to the QDs solution and the mixture is stirred for 16 hours. This solution is further diluted to a final concentration of 0.3 mg/ml. The QY is measured right after the dilution and after 24 hours of storage under ambient conditions.

Example 17

Stability Test by Dilution of InP/ZnS QDs (Red Emitting QDs Manufactured as Described in WO2014/162206 A1 and/or U.S. Pat. No. 9,343,301 BB) after Surface Treatment with Zinc Acetate 25 mg of InP/ZnS (red emitting QDs manufactured as described in WO2014/162206 A1 and/or U.S. Pat. No. 9,343,301 BB) are dissolved in 1 ml toluene (anhydrous grade). The solution is kept under inert atmosphere (Argon). Zinc Acetate (10 mg) (Sigma Aldrich, 99.99% purity) is added to the QDs solution and the mixture is stirred for 16 hours. This solution is further diluted to a final concentration of 0.3 mg/ml. The QY is measured right after the dilution and after 24 hours of storage under ambient conditions.

TABLE 3

QY results from the stability tests by dilution

| Sample | QY measured right after dilution [%] | QY 24 hours after dilution [%] |
|---|---|---|
| EXAMPLE 13 | 45 | 40 |
| EXAMPLE 14 | 52 | 52 |
| EXAMPLE 15 | 75 | 60 |
| EXAMPLE 16 | 70 | 69 |
| EXAMPLE 17 | 75 | 63 |

The results illustrated in Table 3 clearly show a stabilization of QY upon dilution when adding metal thiocarbonate as a ligand according to the invention. Therefore, the metal thiocarbonates not only lead to improvement of QY, they also lead to a stabilization of QY upon dilution and thus to an improvement of emission stability of QDs.

The invention claimed is:

1. A semiconductor nano-sized light emitting material comprising of a core, optionally one or more shell layers and a ligand coated onto the core or the outermost surface of the shell layers,
wherein the ligand is Zn(C18)DTC:

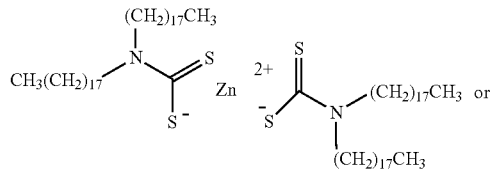

Zn(C18)Xanthate:

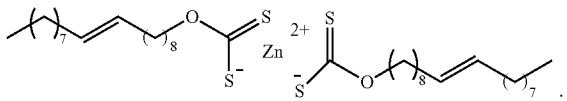

2. The material according to claim 1, wherein said core is formed from one, two or more compounds according to formula (IV), $$[A^1B^1] \quad (IV)$$

in which
[$A^1$] stands for a metal selected from the group consisting of zinc, cadmium, indium or their mixtures;
[$B^1$] stands for a non-metal selected from the group consisting of sulphur, selenium, phosphorous and their mixtures.

3. The material of claim 2, wherein [$A^1B^1$] stands for one, two or more compounds selected from the group consisting of CdS, CdSe, CdSeS, CdZnS, ZnS, ZnSe, ZnSeS, and InP.

4. The material according to claim 1, wherein said shell or said shells are formed from one, two or more compounds according to formula (V), $$[A^2B^2] \quad (V)$$

in which
[$A^2$] stands for a metal selected from the group consisting of zinc, cadmium or their mixtures;
[$B^2$] stands for a non-metal selected from the group consisting of sulphur, selenium, tellurium and their mixtures.

5. The material of claim 4, wherein [$A^2B^2$] stands for one, two or more compounds selected from the group consisting of CdS, CdSe, CdSeS, CdZnS, ZnS, ZnSe and ZnSeS, ZnSeSTe.

6. A composition comprising at least one semiconductor nano-sized light emitting material according to claim 1, and at least one matrix material.

7. A formulation comprising at least one semiconductor nano-sized light emitting material according to claim 1, and at least one solvent.

8. An electronic device, optical device or a biomedical device comprising in said device semiconductor nano-sized light emitting material according to claim 1.

9. An optical medium comprising in said medium the semiconductor nano-sized light emitting material according to claim 1.

10. An optical device comprising said optical medium according to claim 9.

* * * * *